US009999477B2

(12) United States Patent
Takahashi et al.

(10) Patent No.: US 9,999,477 B2
(45) Date of Patent: Jun. 19, 2018

(54) MANIPULATOR SYSTEM

(71) Applicant: OLYMPUS CORPORATION, Tokyo (JP)

(72) Inventors: Keigo Takahashi, Tokyo (JP); Masatoshi Iida, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 13 days.

(21) Appl. No.: 15/004,251

(22) Filed: Jan. 22, 2016

(65) Prior Publication Data

US 2016/0135908 A1 May 19, 2016

Related U.S. Application Data

(63) Continuation of application No. PCT/JP2014/068976, filed on Jul. 17, 2014.

(30) Foreign Application Priority Data

Jul. 26, 2013 (JP) ................................. 2013-155881

(51) Int. Cl.
*A61B 1/005* (2006.01)
*A61B 34/30* (2016.01)
(Continued)

(52) U.S. Cl.
CPC ............ *A61B 34/71* (2016.02); *A61B 1/0051* (2013.01); *A61B 1/0052* (2013.01);
(Continued)

(58) Field of Classification Search
CPC ......... A61B 34/30; A61B 34/35; A61B 34/37; A61B 34/70; A61B 34/71; A61B 34/72;
(Continued)

(56) References Cited

U.S. PATENT DOCUMENTS

2004/0138530 A1 7/2004 Kawai et al.
2007/0078301 A1 4/2007 Kura et al.
(Continued)

FOREIGN PATENT DOCUMENTS

CN 101416867 A 4/2009
EP 2 038 712 B1 8/2011
(Continued)

OTHER PUBLICATIONS

Extended Supplementary European Search Report dated Feb. 7, 2017 in European Patent Application No. 14 82 8977.0.
(Continued)

*Primary Examiner* — Ryan Henderson
(74) *Attorney, Agent, or Firm* — Scully, Scott, Murphy & Presser, P.C.

(57) ABSTRACT

A manipulator system including a manipulator that includes an insertion part having a main section and a bending section, a bending-section driving portion, and a linear member inserted through a sheath fixed to the main section at one end thereof, the linear member connecting the bending section and the bending-section driving portion through the main section and transmitting a driving force generated by the bending-section driving portion to the bending section; an operation input unit via which an operation instruction to the bending section is input; a sheath-tension detecting portion that detects the tension in the sheath; a compensation-value setting portion that sets a compensation value for a bending control signal on the basis of the tension in the sheath, and a control unit that generates the bending control signal and sends the bending control signal corrected with the compensation value to the bending-section driving portion.

7 Claims, 14 Drawing Sheets

(51) Int. Cl.
- *A61B 34/00* (2016.01)
- *A61M 25/01* (2006.01)
- *A61B 34/37* (2016.01)
- *A61B 17/00* (2006.01)
- *B25J 9/10* (2006.01)
- *B25J 9/16* (2006.01)
- *B25J 18/06* (2006.01)
- *G02B 23/24* (2006.01)
- *A61B 90/00* (2016.01)

(52) U.S. Cl.
CPC ............ *A61B 1/0057* (2013.01); *A61B 34/30* (2016.02); *A61B 34/37* (2016.02); *A61B 34/70* (2016.02); *A61M 25/0147* (2013.01); *A61B 34/77* (2016.02); *A61B 2017/00318* (2013.01); *A61B 2017/00323* (2013.01); *A61B 2034/301* (2016.02); *A61B 2034/306* (2016.02); *A61B 2034/715* (2016.02); *A61B 2090/064* (2016.02); *A61B 2090/066* (2016.02); *B25J 9/1045* (2013.01); *B25J 9/1689* (2013.01); *B25J 18/06* (2013.01); *G02B 23/2476* (2013.01)

(58) Field of Classification Search
CPC .............. A61B 34/74; A61B 2034/301; A61B 2034/302; A61B 2034/303; A61B 2034/715; A61B 2034/741; A61B 2034/742; A61B 2034/743; A61B 2034/744; A61B 1/00149; A61B 1/005; A61B 1/0051; A61B 1/0052; A61B 1/0053; A61B 1/0055; A61B 1/0056; A61B 1/0057; A61B 1/0058; A61B 1/008; A61B 1/01; A61M 25/0133; A61M 25/0136; A61M 25/0138; A61M 25/0141; A61M 25/0144; A61M 25/0147; A61M 25/0152; A61M 25/0155; A61M 25/0158; A61M 25/0161
USPC .................. 600/139–152; 604/528; 606/1
See application file for complete search history.

(56) References Cited

U.S. PATENT DOCUMENTS

| | | | |
|---|---|---|---|
| 2007/0112255 A1* | 5/2007 | Ikeda | A61B 1/00039 600/146 |
| 2009/0105726 A1 | 4/2009 | Sugiyama | |
| 2012/0046522 A1 | 2/2012 | Naito | |

FOREIGN PATENT DOCUMENTS

| | | | |
|---|---|---|---|
| EP | 2 517 613 A1 | 10/2012 | |
| JP | 2000-126120 A | 5/2000 | |
| JP | 2000126120 A * | 5/2000 | ........... A61B 1/0057 |
| JP | 2001-198083 A | 7/2001 | |
| JP | 2001-258828 A | 9/2001 | |
| JP | 2002-264048 A | 9/2002 | |
| JP | 2007-089808 A | 4/2007 | |
| JP | 2007-283115 A | 11/2007 | |
| JP | 5048158 B2 | 10/2012 | |

OTHER PUBLICATIONS

International Search Report dated Oct. 7, 2014 issued in PCT/JP2014/068976.

* cited by examiner

MANIPULATOR SYSTEM

CROSS-REFERENCE TO RELATED APPLICATIONS

This is a continuation of International Application PCT/JP2014/068976, with an international filing date of Jul. 17, 2014, which is hereby incorporated by reference herein in its entirety. This application claims the benefit of Japanese Patent Application No. 2013-155881 filed on Jul. 26, 2013, the content of which is incorporated herein by reference.

TECHNICAL FIELD

The present invention relates to manipulator systems.

BACKGROUND ART

In general, an endoscope or a manipulator that is formed of an elongated insertion part, which is to be inserted into an examinee, and an operating part connected at the base end of the insertion part has a bending section at a distal end portion of the insertion part, and the orientation of the distal end can be changed via a bending movement of the bending section. As a mechanism for bending the bending section, a method in which the base end portion of a wire connected to the bending section is pulled by manually turning a knob provided on the operating part is employed. In recent years, research into automation of this bending mechanism has advanced, and techniques for replacing the existing manual knob operation with a motor-driven one have been actively researched (for example, see PTLs 1 and 2). In general, in motor-driven operation, by rotating a motor by an amount proportional to the operation level input to the operating part, the bending angle of the bending section can be changed by an amount of bending corresponding to the operation level.

However, in practice, due to the friction between the wire and a surrounding member, slack in the wire, or a similar reason, the amount of pull applied to the base end portion of the wire is less likely to be fully transmitted to the distal end of the wire. In other words, the amount of pull on the wire and the amount of bending of the bending section have a nonlinear relationship. Moreover, this nonlinearity varies depending on the bending shape of the insertion part. Hence, good and consistent bending-movement responsiveness of the bending section to an operator's operation cannot be obtained by simply making the amount of rotation of the motor proportional to the operation level.

To counter this problem, in PTLs 1 and 2, focusing on the amount of travel of the wire or the tension in the wire, serving as an indicator of the bending shape of the bending section or main section, which is a cause of the degradation in the bending-movement responsiveness of the bending section, the motor is controlled such that the degradation and variation in the responsiveness of the bending section are compensated for on the basis of the amount of travel of the wire or the tension in the wire, thus improving the responsiveness.

Besides the bending shape of the bending section or main section described above, there are other causes of the degradation in the bending-movement responsiveness of the bending section.

CITATION LIST

Patent Literature

{PTL 1} Japanese Unexamined Patent Application, Publication No. 2002-264048
{PTL 2} The Publication of Japanese Patent No. 5048158

SUMMARY OF INVENTION

The present invention provides a manipulator system including a manipulator that includes an insertion part having an elongated main section and a bending section provided at the distal end of the main section, a bending-section driving portion that makes the bending section perform bending movement, and a linear member inserted through a tubular sheath that is fixed to the main section at at least one end thereof, the linear member connecting the bending section and the bending-section driving portion through the main section and transmitting a driving force generated by the bending-section driving portion to the bending section; an operation input unit via which an operator inputs an operation instruction for the bending section; a control unit that generates a bending control signal for driving the bending-section driving portion according to the operation instruction input to the operation input unit; a sheath-tension detecting portion that detects the tension in the sheath; and a compensation-value setting portion that sets a compensation value for the bending control signal on the basis of the tension in the sheath detected by the sheath-tension detecting portion. The control unit corrects the bending control signal using the compensation value set by the compensation-value setting portion and sends the corrected bending control signal to the bending-section driving portion.

DESCRIPTION OF EMBODIMENTS

First Embodiment

A manipulator system 100 according to a first embodiment of the present invention will be described with reference to FIGS. 1 to 8.

Figure 1:
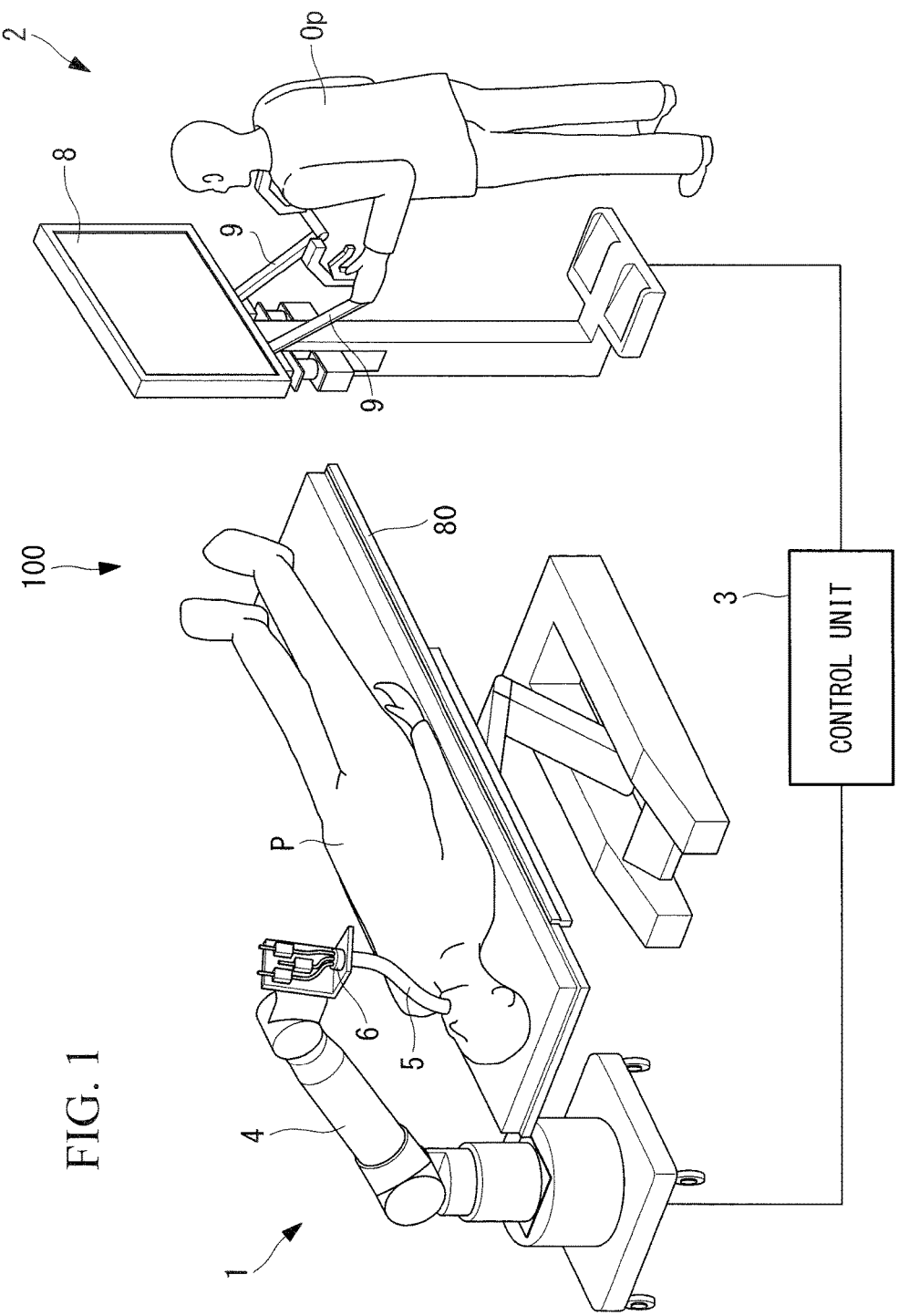
FIG. 1 is a diagram showing the basic configuration of a manipulator system according to a first embodiment of the present invention.

First, an outline of the manipulator system 100 according to this embodiment will be described. As shown in FIG. 1, the manipulator system 100 according to this embodiment includes, as a main configuration, a slave manipulator (manipulator) 1, a master input unit (operation input unit) 2 to be operated by an operator (operator) Op, and a control unit 3 for controlling the slave manipulator 1 on the basis of the operation performed on the master input unit 2.

Figure 2:
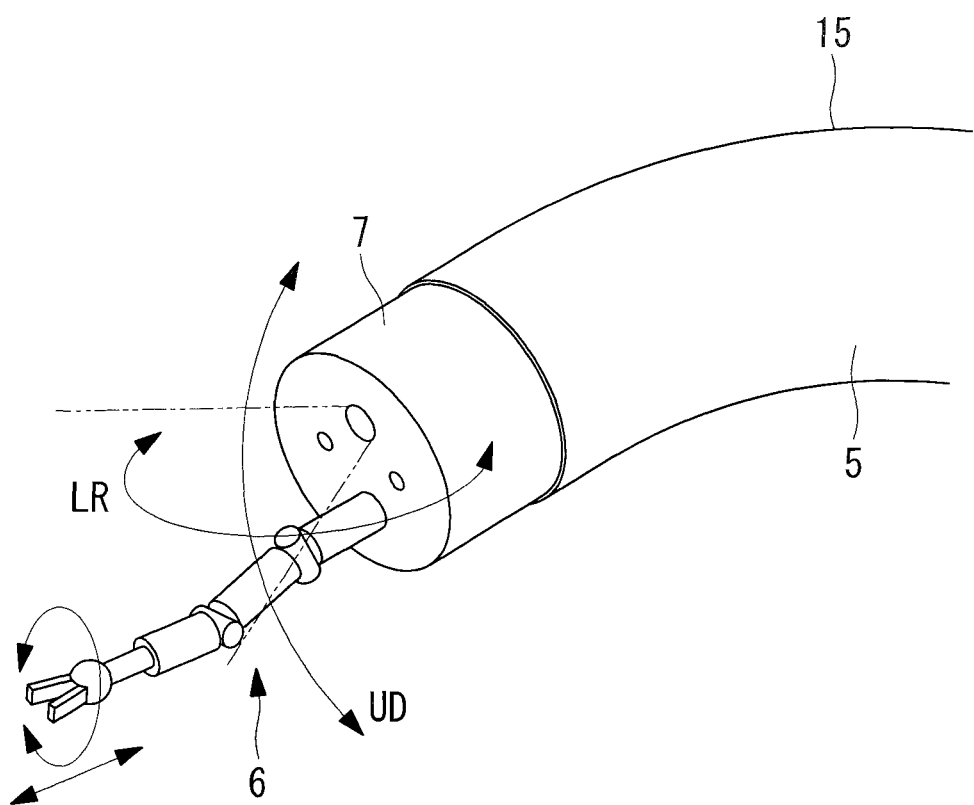
FIG. 2 is a diagram showing the configuration of a distal end portion of an insertion part provided in the manipulator system in FIG. 1.

The slave manipulator 1 includes a slave arm 4 positioned near an operating table 80 on which a patient P lies, an insertion part 5 held at the distal end of the slave arm 4, and a treatment tool 6 inserted into the insertion part 5. As shown in FIG. 2, an observation member 7 is provided at the distal end of the insertion part 5, and an image of the field of view in front of the distal end of the insertion part 5 and the treatment tool 6 projecting from the distal end of the insertion part 5 is acquired by the observation member 7. The image acquired by the observation member 7 is displayed on a display 8 provided in the master input unit 2. The field of view of the observation member 7 can be moved by changing the bending angle of a bending section 15 provided at the distal end portion of the insertion part 5 in the up-down direction (UD direction) or the left-right direction (LR direction) perpendicular to the longitudinal direction of the insertion part 5.

The operator Op can, by operating master arms 9 provided in the master input unit 2, remote-control the insertion part 5 inserted into the body of the patient P and the treatment tool 6 inserted into the body through the insertion part 5, while observing the image of the body and the treatment tool 6 displayed on the display 8.

Next, the respective components of the manipulator system 100 will be described in detail.

Figure 3:
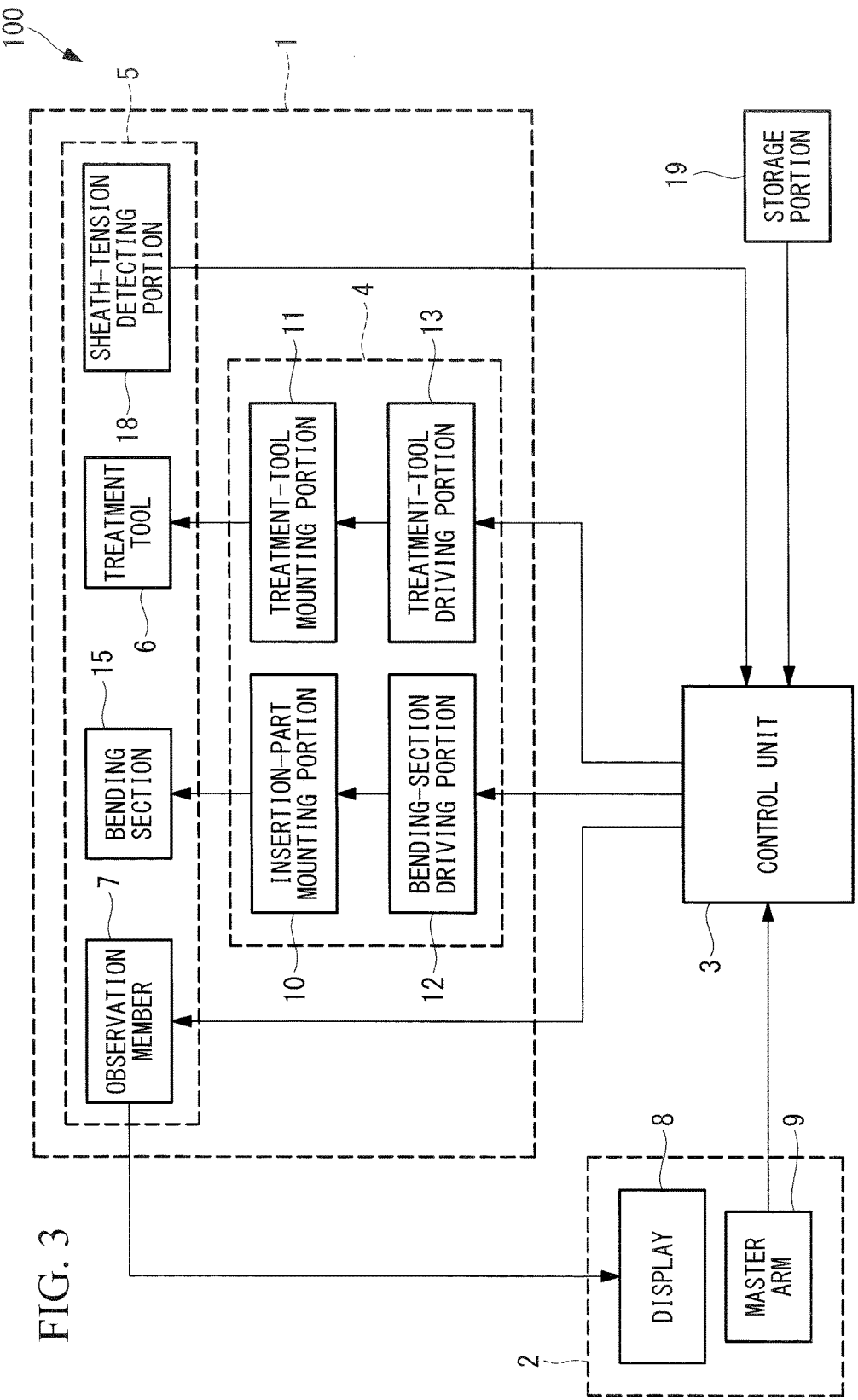
FIG. 3 is a block diagram showing the overall configuration of the manipulator system in FIG. 1.

As shown in FIG. 3, the slave arm 4 includes an insertion-part mounting portion 10 to which the insertion part 5 is mounted, a treatment-tool mounting portion 11 to which the treatment tool 6 is mounted, a bending-section driving portion 12 for driving the bending section 15 of the insertion part 5 mounted to the insertion-part mounting portion 10, and a treatment-tool driving portion 13 for driving the treatment tool 6 mounted to the treatment-tool mounting portion 11. The bending-section driving portion 12 and the treatment-tool driving portion 13 drive the corresponding one of the bending section 15 and the treatment tool 6 according to the control signals received from the control unit 3.

Figure 4:
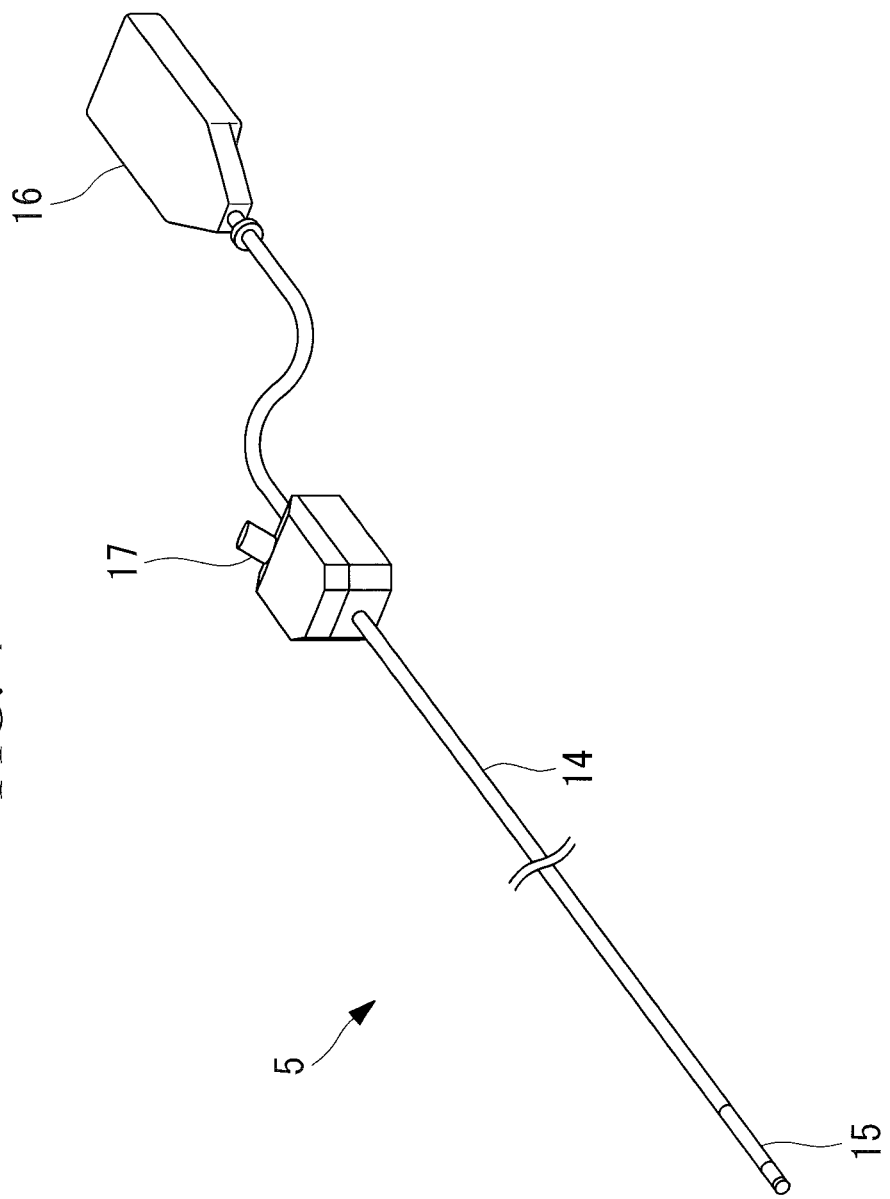
FIG. 4 is a diagram showing the overall configuration of the insertion part provided in the manipulator system in FIG. 1.

FIG. 4 shows the appearance of the insertion part 5. As shown in FIG. 4, the insertion part 5 includes an elongated flexible main section 14 and the bending section 15 provided at the distal end of the main section 14. Furthermore, a mounting unit 16 to be mounted to the insertion-part mounting portion 10 of the slave arm 4 is coupled to the base end of the main section 14. The bending section 15 has a known structure in which a plurality of segment rings or bending pieces are connected. The bending section 15 is configured to be bent in the UD direction or the LR direction in response to the base end portions of a wire (linear member) 15a, corresponding to bending in the UD direction, and a wire (linear member) 15b, corresponding to bending in the LR direction, connected to the segment ring or the like on the extreme distal-end side being pushed or pulled in the longitudinal direction, inside the mounting unit 16.

Figure 5:
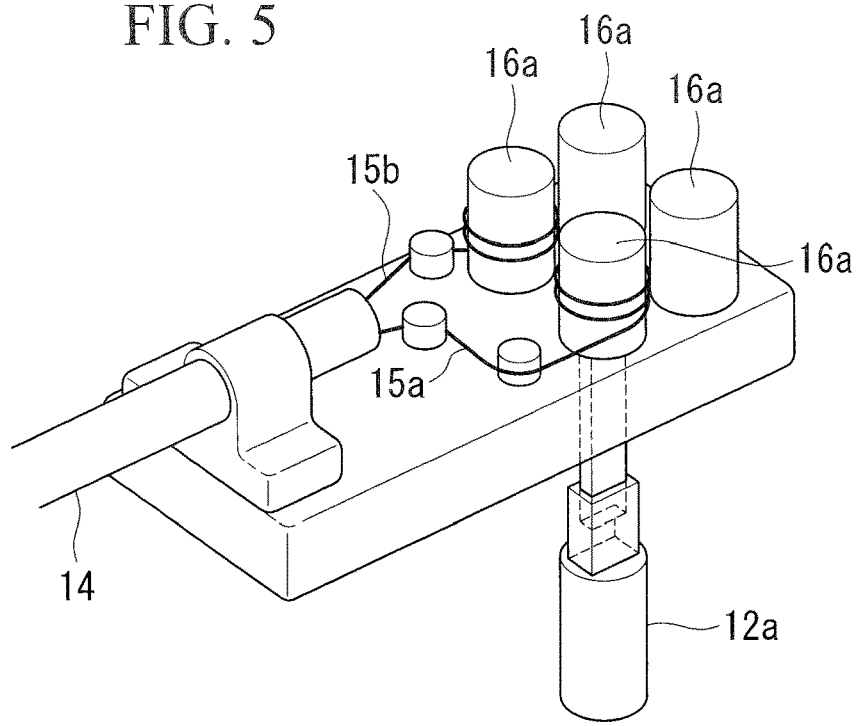
FIG. 5 is a configuration diagram showing a mechanism for bending a bending section in FIG. 4.

More specifically, as shown in FIG. 5, the base end portions of the wires 15a and 15b are led out of the base end of the main section 14 and are wound around pulleys 16a provided in the mounting unit 16. The mounting unit 16 is configured such that, when mounted to the insertion-part mounting portion 10, the pulleys 16a and motors 12a provided in the bending-section driving portion 12 are coaxially connected. When the motors 12a are rotated according to rotation control signals from the control unit 3, the pulleys 16a are rotated forward or reversely, whereby the wires 15a and 15b are pushed or pulled, changing the bending angle of the bending section 15. Note that, to simplify the figure, FIG. 5 shows only one motor 12a. Furthermore, only the wire 15b is shown in a state in which it is wound around the pulley 16a.

Figure 6:
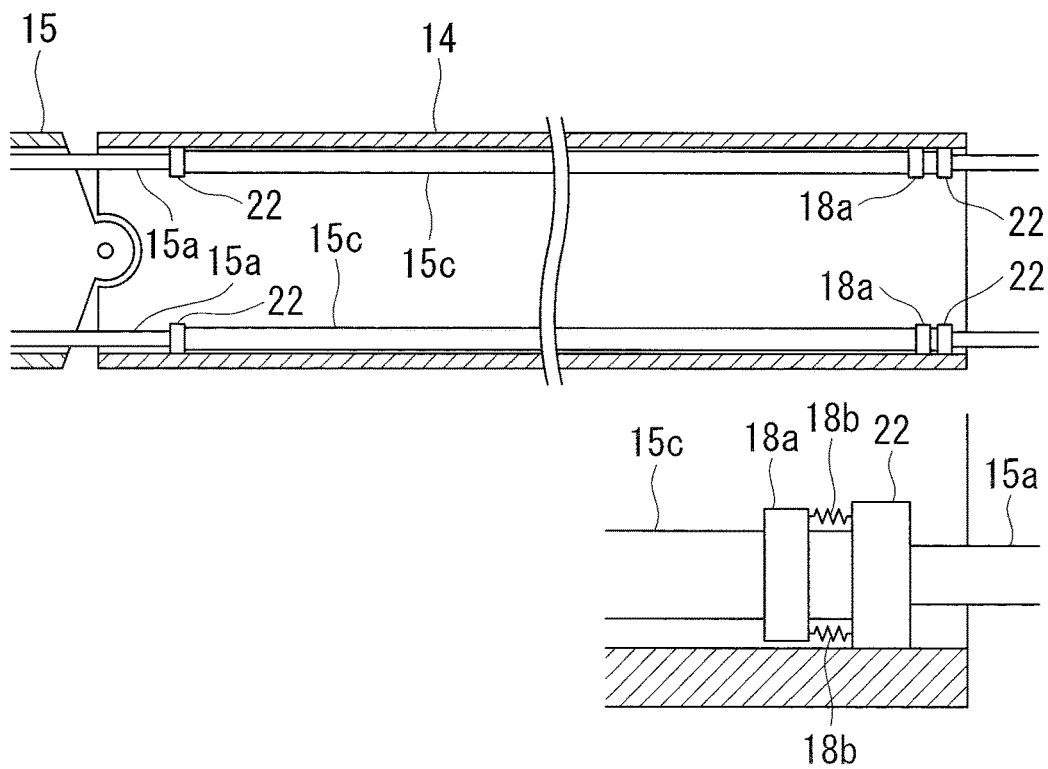
FIG. 6 includes a configuration diagram (upper side) showing a wire and a wire sheath provided in the insertion part in FIG. 4, and an enlarged view (lower diagram) showing the configuration of a tension sensor provided in the wire sheath.

As shown in FIG. 6, tubular wire sheaths (sheath) 15c, through which the wire 15a and 15b pass, are provided on the outer side of the wires 15a and 15b. The wire sheaths 15c are coil sheaths formed by winding an element wire in a spiral configuration. The distal ends of the wire sheaths 15c are fixed to the distal end of the main section 14 or the vicinity thereof by fixing portions 22, and the base ends of the wire sheaths 15c are fixed to the base end of the main section 14 or the vicinity thereof by the fixing portions 22. Due to the path lengths of the wire sheaths 15c being changed in response to a change in bending shape of the main section 14, the wire sheaths 15c produce tension corresponding to the bending shape of the main section 14.

Furthermore, the insertion part 5 has a channel (not shown) formed so as to penetrate in the longitudinal direction. This channel communicates with a treatment tool port 17 provided at the base end of the insertion part 5, and the treatment tool 6 is inserted into the channel from the treatment tool port 17. Examples of the treatment tool 6 include a high-frequency knife, a snare loop, and a grasping forceps. A mounting unit (not shown) mounted to the treatment-tool mounting portion 11 of the slave arm 4 is connected to the base end of the treatment tool 6. The treatment tool 6 is provided such that it can be advanced, retracted, or rotated in the channel by being driven by the treatment-tool driving portion 13 via the mounting unit and the treatment-tool mounting portion 11. Although FIG. 2 shows the insertion part 5 having a single channel, two or more channels may be provided in the insertion part 5.

As described above, the master input unit 2 includes the display 8 for displaying the image acquired by the observation member 7, and the plurality of master arms 9 operated by the operator Op. The master arms 9 allow the operator Op to input operation instructions for, at least, the bending section 15 and the treatment tool 6. The master input unit 2 generates operation signals according to the operation instructions input to the master arms 9 by the operator Op and sends the generated operation signals to the control unit 3.

When receiving an operation signal for the bending section 15 from the master input unit 2, the control unit 3 generates, from the operation signal, a bending control signal for driving the bending-section driving portion 12 and sends the bending control signal to the bending-section driving portion 12. Furthermore, when receiving an operation signal for the treatment tool 6 from the master input unit 2, the control unit 3 generates, from the operation signal, an advancing-or-retracting control signal and a rotation control signal for driving the treatment-tool driving portion 13 and sends the advancing-or-retracting control signal and the rotation control signal to the treatment-tool driving portion 13. The motors 12a for the respective driving parts 12 and 13 are provided with an encoder (not shown) for detecting the amount of rotation thereof. The control unit 3 identifies the amount of bending of the bending section 15 and the amounts of advancement, retraction, or rotation of the treatment tool 6 by receiving the amount of rotation of the motors 12a from the encoder, and feedback (FB)-controls the motors 12a for the respective driving parts 12 and 13 on the basis of these identified amounts.

Moreover, the manipulator system 100 according to this embodiment includes a sheath-tension detecting portion 18 that detects the tension (hereinbelow, also referred to as "sheath tension") in the wire sheaths 15c and includes a storage portion 19.

The sheath-tension detecting portion 18 includes tension sensors 18a attached to the wire sheaths 15c, and the sheath-tension detecting portion 18 measures the sheath tension with the tension sensors 18a and sends the measurement values to the control unit 3.

More specifically, as shown in the lower side in FIG. 6, the tension sensors 18a are coupled to the fixing portions 22 with springs 18b therebetween and detect a change in the sheath tension in the wire sheaths 15c due to deformation of portions between the tension sensors 18a and the fixing portions 22, in the form of a change in force applied from the springs 18b. The position at which the tension sensors 18a are mounted is not specifically limited, but the base end portion of the wire sheaths 15c is preferable. At the base end portion of the wire sheaths 15c, a space for mounting the tension sensors 18a can be easily ensured without affecting the other configurations.

The storage portion 19 stores a table of sheath tensions and associated compensation values for bending control signals. The compensation value is a feedforward gain by which the bending control signal is multiplied, and, as will be described in detail below, the compensation value is set so as to increase with a decrease in sheath tension, on the basis of the correlation between the sheath tension and the responsiveness of the bending section 15. The storage portion 19, upon receipt of a sheath-tension measurement value from the control unit 3, selects a compensation value corresponding to the measurement value and sends the selected compensation value to the control unit 3.

Herein, the control unit (compensation-value setting portion) 3, upon receipt of an operation signal for the bending section 15 from the master input unit 2, acquires a compensation value for the bending control signal from the storage portion 19 according to the following steps, before sending the bending control signal to the bending-section driving portion 12. First, the control unit 3 sends a data-transmission order to the sheath-tension detecting portion 18. Upon receipt of the data-transmission order, the sheath-tension detecting portion 18 measures the sheath tension and sends the measurement value to the control unit 3. Then, the control unit 3 sends the measurement value received from the sheath-tension detecting portion 18 to the storage portion 19 and receives the compensation value corresponding to the measurement value from the storage portion 19. Thereafter, the control unit 3 amplifies the bending control signal by multiplying the bending control signal generated from the operation signal by the compensation value and sends the amplified bending control signal to the bending-section driving portion 12, thereby feedforward-controlling the bending-section driving portion 12.

Next, the operation of the thus-configured manipulator system 100 will be described.

When inside of the body is treated by using the manipulator system 100 according to this embodiment, as shown in FIG. 1, the operator Op first inserts the insertion part 5 into the body from a natural opening (mouth, in the example shown) of the patient P. The operator Op moves the distal end of the insertion part 5 to a target site, while observing, with the display 8, the image acquired by the observation member 7.

The operator Op then causes the treatment tool 6 inserted in the channel in the insertion part 5 to project from the opening in the distal end of the insertion part 5. Subsequently, the operator Op, while observing the image displayed on the display 8, adjusts the positional relationship between the treatment tool 6 and the target site in the body by changing the bending angle of the bending section 15 and the amount of projection and the rotation direction of the treatment tool 6 and treats the target site with the treatment tool 6.

At this time, when the operator Op inputs an operation for changing the bending angle of the bending section 15 to the master arms 9, an operation signal corresponding to this operation is sent from the master arms 9 to the control unit 3. The control unit 3 generates a bending control signal for causing the bending section 15 to bend in the LR direction or the UD direction, according to the received operation signal. Meanwhile, the control unit 3 causes the sheath-tension detecting portion 18 to measure the sheath tension at this moment and acquires the compensation value corresponding to the acquired sheath tension from the storage portion 19. The control unit 3, by sending the bending control signal, amplified by the compensation value, to the bending-section driving portion 12, actuates the bending section 15.

Now, the relationship between the bending-movement responsiveness of the bending section 15 to the operation input to the master arms 9 by the operator Op and the sheath tension will be described.

Figure 7:
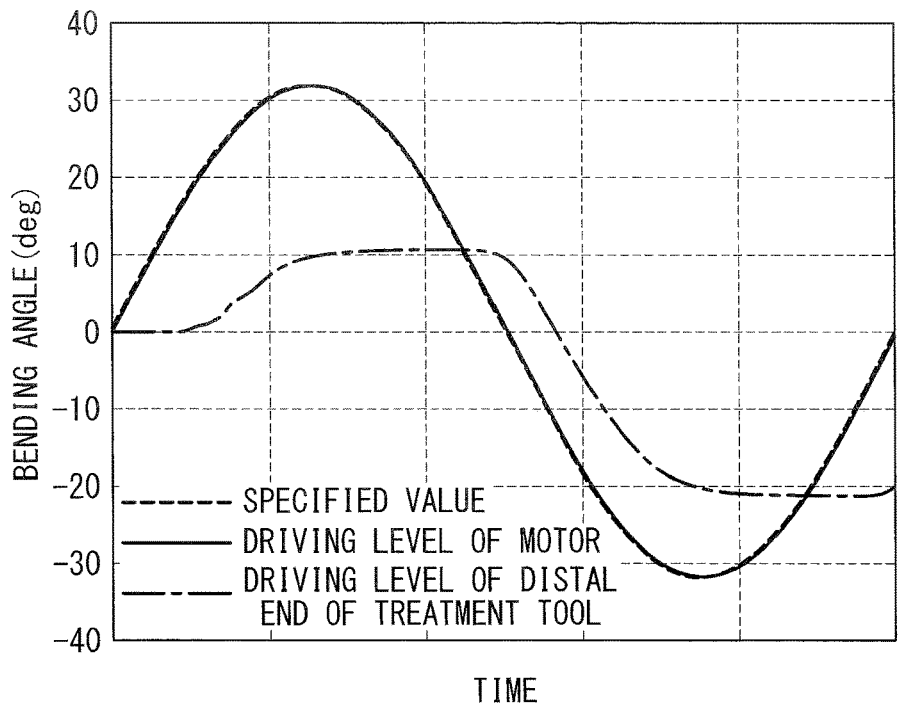
FIG. 7 is a graph showing the responsiveness of the bending section in response to an operation signal, in a state in which the sheath tension is low.
Figure 8:
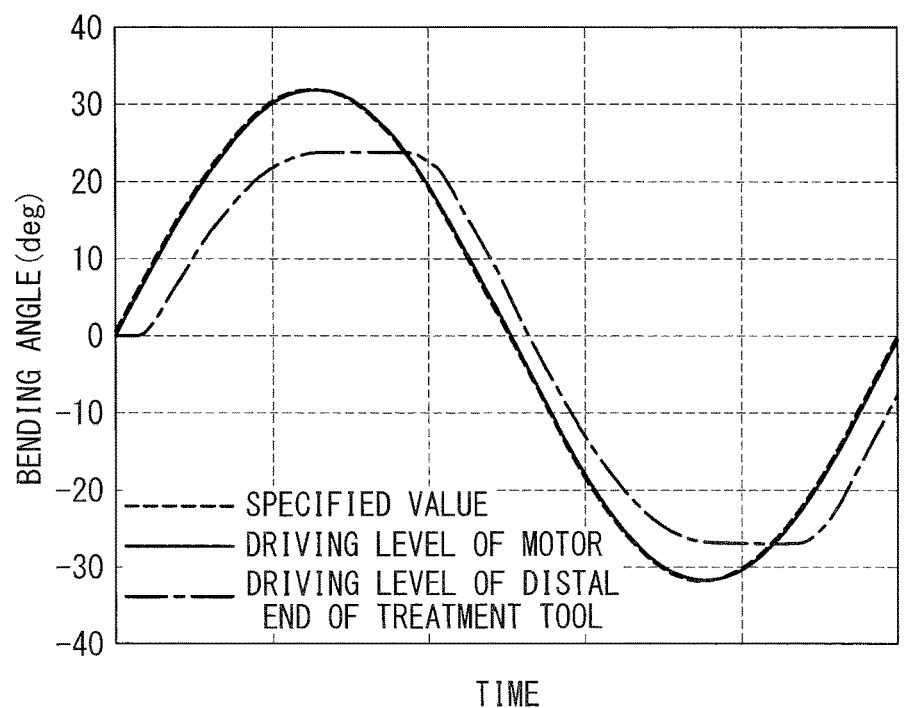
FIG. 8 is a graph showing the responsiveness of the bending section in response to an operation signal, in a state in which the sheath tension is high.

FIGS. 7 and 8 show the responsiveness of the bending section 15 to the operation signal. FIG. 7 shows the responsiveness when the sheath tension is relatively low, and FIG. 8 shows the responsiveness when the sheath tension is relatively high. In FIGS. 7 and 8, the dashed line indicates the bending angle specified by the operation signal input to the control unit 3, the solid line indicates the driving level of the motors 12a calculated from the output of the encoder provided on the bending-section driving portion 12, and the one-dot chain line indicates the driving level of the distal end of the treatment tool 6 caused by bending of the bending section 15.

As can be seen from FIG. 7, when the sheath tension is relatively low, the driving level of the distal end of the treatment tool 6 is small relative to the operation signal and the driving level of the motors 12a. In the example in FIG. 7, only about 30% of the tensile force applied to the base end portion of the wire 15a or 15b is consumed by the bending movement of the bending section 15, and the rest, about 70% of the tensile force, is consumed by factors other than the bending movement of the bending section 15.

In contrast, as can be seen from FIG. 8, when the sheath tension is relatively high, the bending-movement responsiveness of the bending section 15 is large relative to the operation signal and the driving level of the motors 12a. In the example in FIG. 8, about 75% of the tensile force applied to the base end portion of the wire 15a or 15b is consumed by the bending movement of the bending section 15, and the rest, about 25% of the tensile force, is consumed by factors other than the bending movement of the bending section 15.

As described above, there is a strong correlation between the responsiveness of the bending section 15 to the operation signal and the sheath tension; the higher the sheath tension is, the higher the responsiveness of the bending section 15 is. The compensation values recorded in the storage portion 19 are set so as to compensate for the variations in the responsiveness of the bending section 15, which depend on the level of the sheath tension.

The reason why the responsiveness of the bending section 15 is higher when the sheath tension is higher is assumed to be that the friction generated between the wire sheaths 15c and the wires 15a and 15b is smaller when the sheath tension is higher.

According to this embodiment, focusing on the fact that a change in the sheath tension associated with a change in bending shape of the main section 14 is a major cause of the degradation and variation in the responsiveness of the bending section 15, the bending-section driving portion 12 is feedforward-controlled on the basis of the sheath tension. This leads to an advantage that it is possible to precisely compensate for the degradation and variation in the bending-movement responsiveness of the bending section 15 and to constantly obtain good and consistent responsiveness of the bending section 15.

Note that, when the main section 14 is bent, the sheath tension varies among the wire sheaths 15c due to the difference in the path length between the wire sheath 15c on the inner circumferential side of the bending shape and that on the outer circumferential side.

Thus, it is preferable that the tension sensor 18a be attached to each of the wire sheaths 15c and that the control unit 3 individually set a compensation value for each of the motors 12a. By doing so, it is possible to more precisely compensate for the variation in the bending-movement responsiveness of the bending section 15.

Furthermore, although the compensation value has been described as being a feedforward gain in this embodiment, another compensation value may be used instead.

For example, the compensation value may be a feedback gain that is used by the control unit 3 to feedback-control the bending-section driving portion 12.

As described above, the control unit 3 feedback-controls the motors 12a on the basis of the amount of rotation of the motors 12a detected by the encoder. Hence, the control unit 3 may set the feedback gain on the basis of the sheath tension. Also in this way, it is possible to precisely compensate for the degradation and variation in the responsiveness of the bending section 15, which depend on the bending shape of the main section 14 and the difference in sheath tension.

Alternatively, the compensation value may be a friction compensation coefficient (offset signal) to be added to the bending control signal by the control unit 3 to give an offset to the bending control signal. The friction compensation coefficient is set such that the sign is reversed at a turning portion where the direction of the bending movement of the bending section 15 is changed in the opposite direction. By doing so, particularly, a backlash occurring when the direction of the bending movement is changed to the opposite direction (for example, when changed from the L direction to the R direction) can be suppressed.

Second Embodiment

Next, a manipulator system according to a second embodiment of the present invention will be described with reference to FIGS. 9A to 11B.

A manipulator system according to this embodiment differs from that in the first embodiment in the configuration of the insertion part 5. Hence, in this embodiment, the configuration of the insertion part 5 will be mainly described, the components common to those of the first embodiment will be denoted by the same reference signs, and the descriptions thereof will be omitted.

Figure 9A:
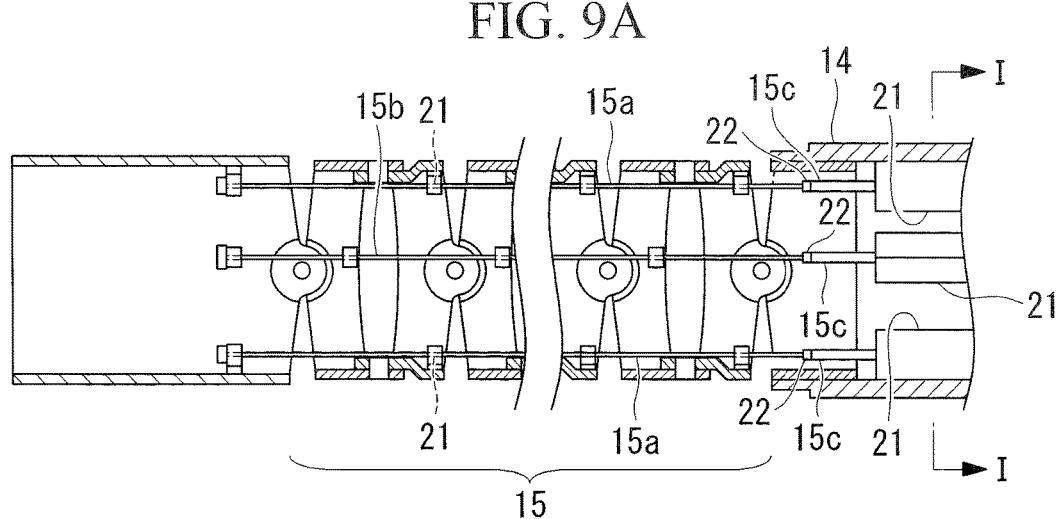
FIG. 9A is a partial longitudinal cross-sectional view of an insertion part provided in a manipulator system according to a second embodiment of the present invention.
Figure 9B:
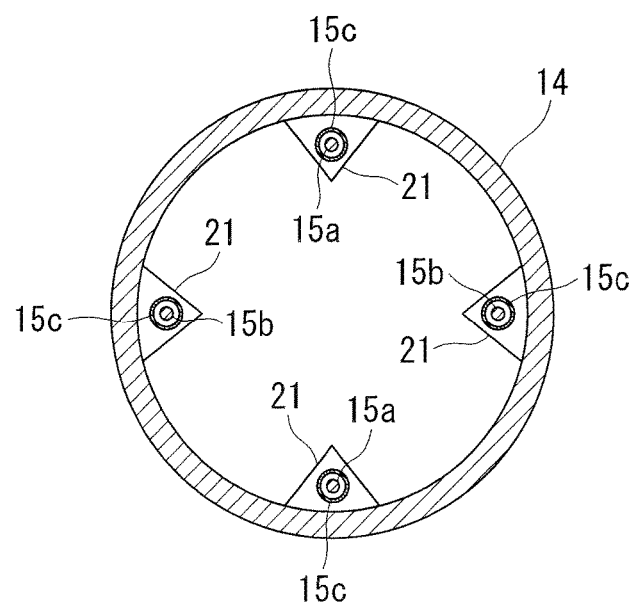
FIG. 9B is a lateral cross-sectional view of the insertion part in FIG. 9A, taken along line I-I.

In this embodiment, as shown in FIGS. 9A and 9B, passages 21 that define the positions of the wires 15a and 15b are formed in the main section 14 and the bending section 15. In the bending section 15, these passages 21 are formed of ring-shaped members fixed to the inner circumferential surfaces of the segment rings. In the main section 14, these passages 21 are spaces that are formed so as to penetrate in the longitudinal direction of the main section 14 and that are isolated from the space where members other than the wires 15a and 15b are disposed.

If the wires 15a and 15b are freely movable in the radial direction inside the main section 14 and the bending section 15, even though the bending shape of the main section 14 is the same, the optimum compensation values may vary. This is because the friction and slack in the wires 15a and 15b may vary due to variations in the paths of the wires 15a and 15b. Hence, by defining the paths of the wires 15a and 15b inside the main section 14 and the bending section 15 with the passages 21 and preventing the wires 15a and 15b from randomly coming into contact with other members, it is possible to more precisely compensate for the degradation and variation in the bending-movement responsiveness of the bending section 15. Because the other advantages are the same as those obtained according to the first embodiment, the descriptions thereof will be omitted.

Figure 10A:
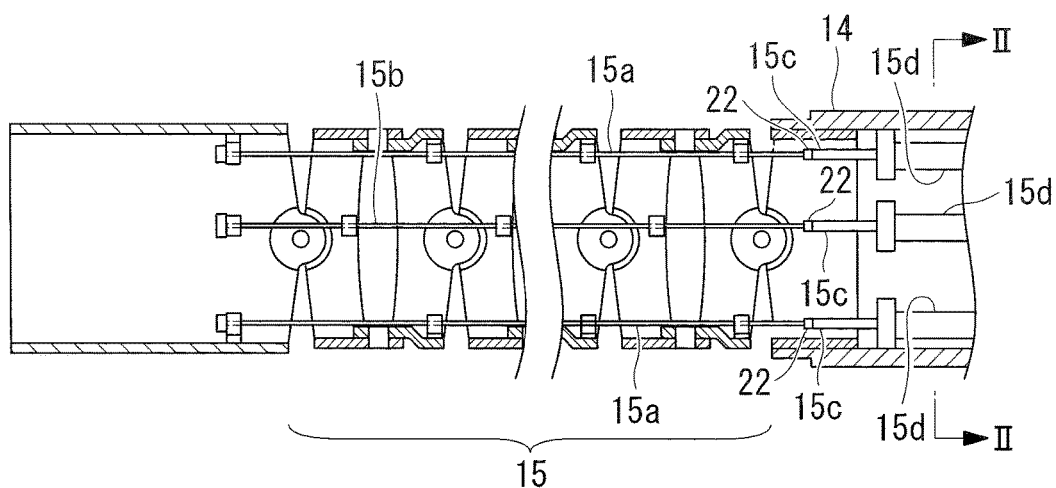
FIG. 10A is a partial longitudinal cross-sectional view showing a modification of the insertion part in FIG. 9A.
Figure 10B:
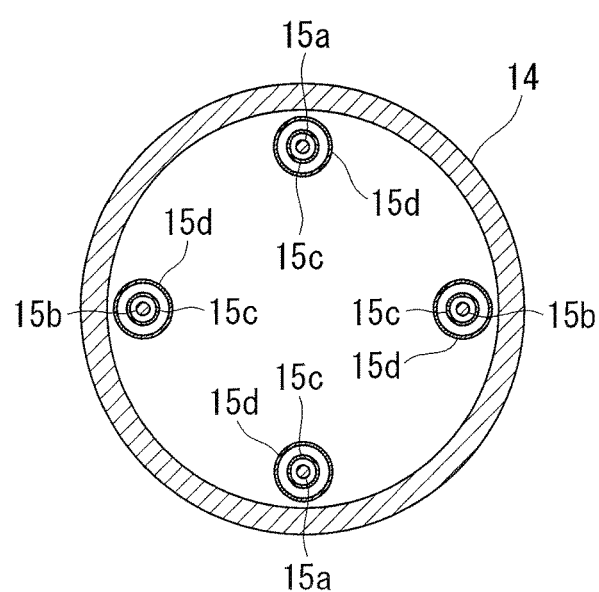
FIG. 10B is a lateral cross-sectional view of the insertion part in FIG. 10A, taken along line II-II.

Note that, although the passages 21 for the wires 15a and 15b are provided in the main section 14 in this embodiment, instead, as shown in FIGS. 10A and 10B, outer sheaths 15d that accommodate the wire sheaths 15c may be provided.

Also with this configuration, it is possible to prevent the wire sheaths 15c from randomly coming into contact with various members therearound and to more precisely compensate for the degradation and variation in the bending-movement responsiveness of the bending section 15.

Figure 11A:
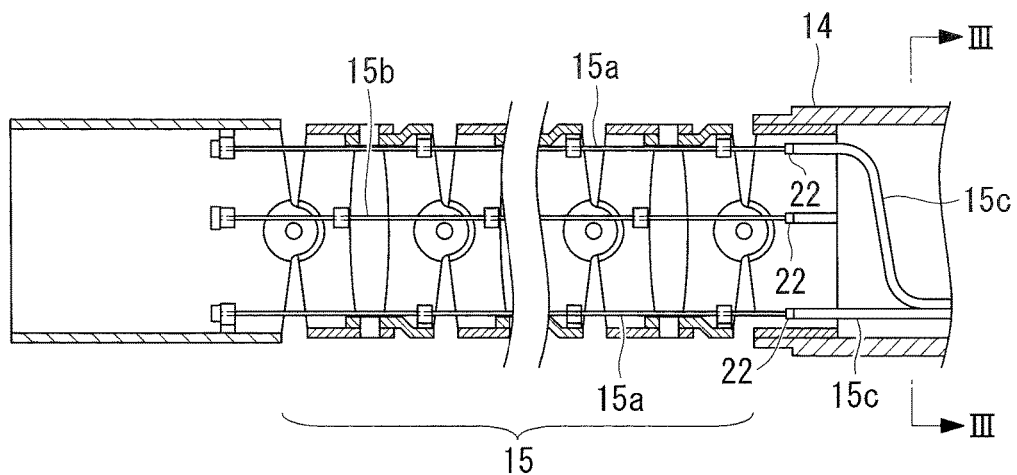
FIG. 11A is a partial longitudinal cross-sectional view showing another modification of the insertion part in FIG. 9A.
Figure 11B:
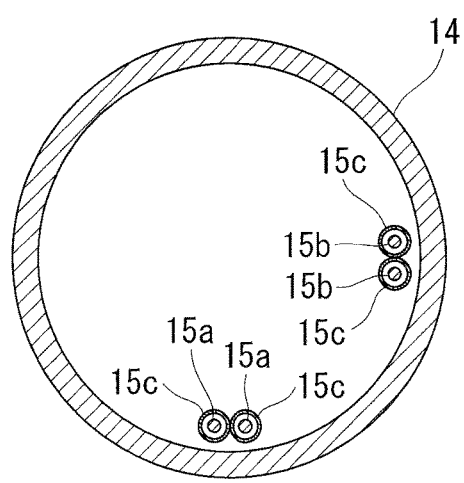
FIG. 11B is a lateral cross-sectional view of the insertion part in FIG. 11A, taken along line

Furthermore, in this embodiment, as shown in FIGS. 11A and 11B, the plurality of wires 15a and 15b may be bound together via the wire sheaths 15c, inside the main section 14. By doing so, a variation, among the wire sheaths 15c, in the tension generated in the wire sheaths 15c can be reduced.

Hence, even when the same compensation value is used for the motors 12a, it is possible to compensate for the variation in the responsiveness of the bending section 15 with sufficient precision, making the control of the plurality of motors 12a easy.

Third Embodiment

Figure 12:
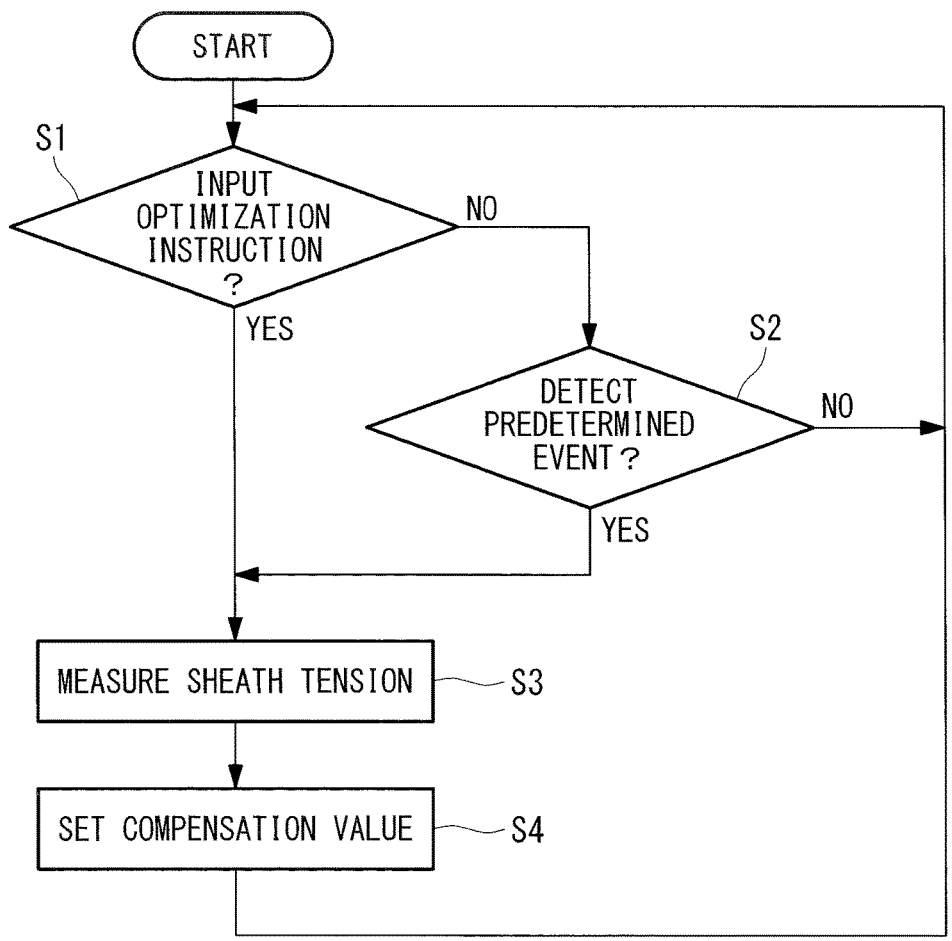
FIG. 12 is a flowchart showing a method for setting a compensation value with a manipulator system according to a third embodiment of the present invention.

Next, a manipulator system according to a third embodiment of the present invention will be described with reference to FIGS. 12 and 13.

The manipulator system according to this embodiment differs from those according to the first and second embodiments in the details of the control associated with setting of the compensation values by the control unit 3. Hence, in this embodiment, the details of the control by the control unit 3 will be mainly described, the components common to those of the first embodiment will be denoted by the same reference signs, and the descriptions thereof will be omitted.

This embodiment differs from the first embodiment in that the measurement of the sheath tension and the setting of the compensation value are performed at intended or predetermined timing specified by the operator Op. FIG. 12 shows an operation related to setting of the compensation value in the manipulator system according to this embodiment.

When an optimization instruction is input to the master input unit 2 (YES in step S1), the control unit 3 makes the sheath-tension detecting portion 18 measure the sheath tension (step S3) and sets a compensation value (step S4). In this way, the operator Op can optimize the compensation value at an intended timing when good bending-movement responsiveness of the bending section 15 is needed. The optimization instruction is input to the master input unit 2 by, for example, the operator pressing a button provided on the master input unit 2.

Furthermore, when a predetermined event is detected (YES in step S2), the control unit 3 makes the sheath-tension detecting portion 18 measure the sheath tension (step S3) and sets a compensation value (step S4). The predetermined event is an event that may change the sheath tension, such as a change in body position of the patient P on the operating table 80, a movement of an organ, or the like. In this way, when a predetermined event that may change the sheath tension occurs, the compensation value can be automatically optimized. A change in body position of the patient P may be detected on the basis of, for example, the weight distribution on the operating table 80. A movement of an organ may be detected by using, for example, image recognition and on the basis of a sudden change of an image in the image acquired by the observation member 7. Furthermore, the event may be an input from the outside, such as pressing of a button (not shown) by the operator Op.

As described above, according to this embodiment, by measuring the sheath tension and by optimizing the compensation value in the case where good bending-movement responsiveness of the bending section 15 is particularly required or in the case where a change in responsiveness of the bending section 15 may occur, an advantage is obtained in that the amount of processing required to set the compensation value can be reduced to a necessary and sufficient amount. Because the other advantages are the same as those obtained according to the first embodiment, the descriptions thereof will be omitted.

Although the sheath tension is measured at an intended or predetermined timing in this embodiment, instead, the sheath tension may be constantly measured, and the compensation value may be intermittently reset on the basis of the amount of change in the sheath tension.

Figure 13:
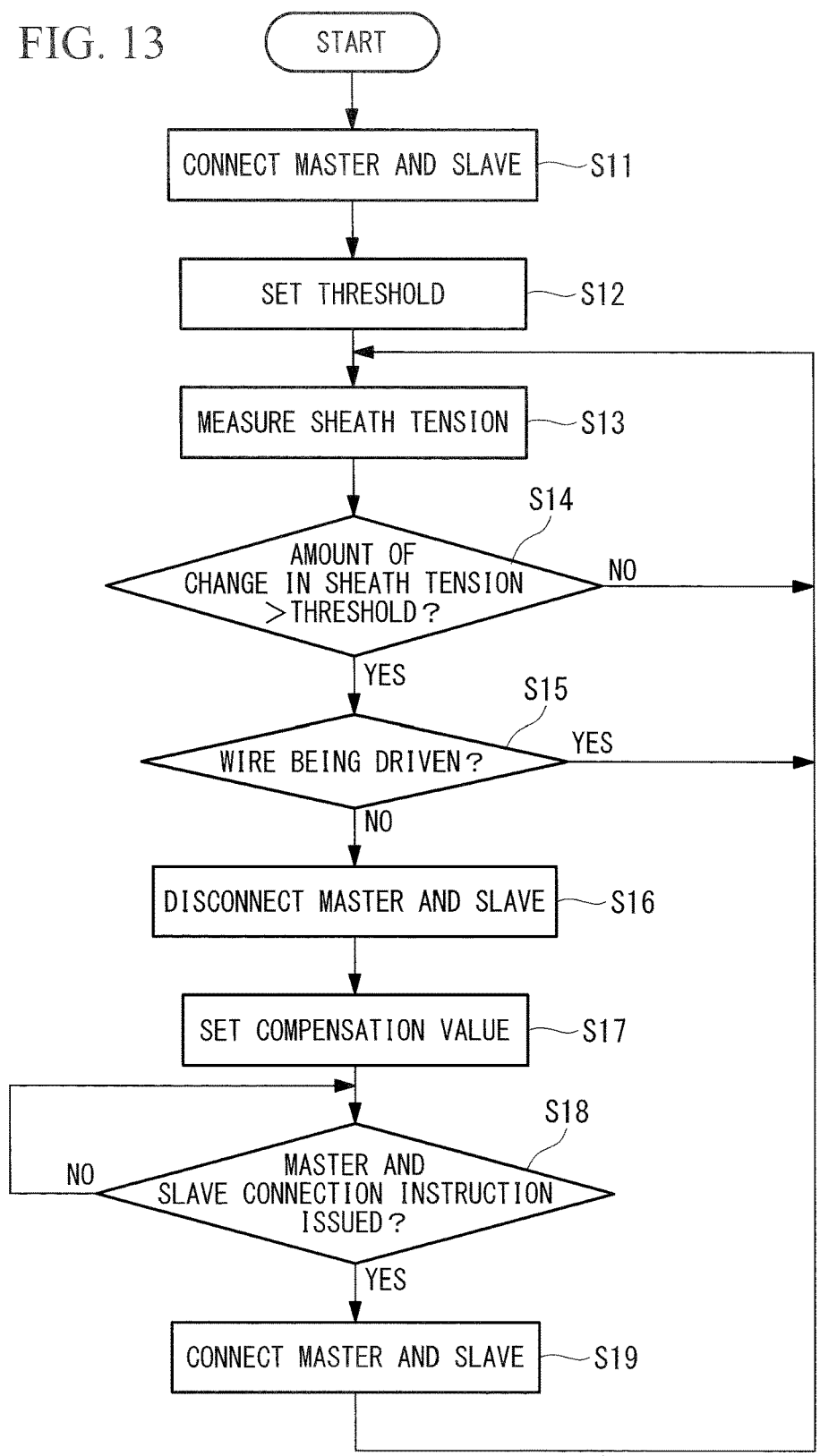
FIG. 13 is a flowchart showing a modification of the method for setting a compensation value in FIG. 12.

For example, as shown in FIG. 13, after the operation of the insertion part 5 is started (step S11), a threshold of the amount of change in the sheath tension is set (step S12), and the sheath tension is constantly measured (step S13). Then, when the amount of change in the sheath tension has exceeded the threshold (YES in step S14), the communication between the master input unit 2 and the slave arm 4 is cut off (step S16), and a compensation value is set on the basis of the latest sheath-tension measurement value (step S17). More specifically, a situation in which the amount of change in the sheath tension has exceeded the threshold is detected as the event.

However, even if the amount of change in the sheath tension has exceeded the threshold in step S14, while the wires 15a and 15b are being driven by the motors 12a (YES in step S15), the compensation value is not reset until driving of the wires 15a and 15b is completed. Because the sheath tension changes independently of the shape of the insertion part 5 while the wires 15a and 15b are driven, even if a change in the sheath tension exceeding the threshold is detected while the wires 15a and 15b are driven, such a change is not taken into account. After the compensation value is set, according to the instruction from the operator Op (step S18), the communication between the master input unit 2 and the slave arm 4 is reconnected (step S19).

By doing so, when the sheath tension changes with time according to the change in the bending shape of the main section 14, the compensation value is optimized so as to follow the change in the sheath tension with time. Thus, it is possible to reduce the amount of processing required to set the compensation value, while maintaining good bending-movement responsiveness of the bending section 15. Furthermore, by cutting the communication between the master input unit 2 and the slave arm 4 when the compensation value is reset, the compensation value can be reliably reset.

Fourth Embodiment

Next, a manipulator system according to a fourth embodiment of the present invention will be described with reference to FIGS. 14 to 16.

The manipulator system according to this embodiment differs from those according to the first to third embodiments in that the sheath-tension detecting portion 18 includes a sheath-tension adjusting mechanism 20 that adjusts the tension produced in the wire sheaths 15c. Hence, in this embodiment, the sheath-tension adjusting mechanism 20 will be mainly described, the components common to those of the first to third embodiments will be denoted by the same reference signs, and the descriptions thereof will be omitted.

Figure 14:
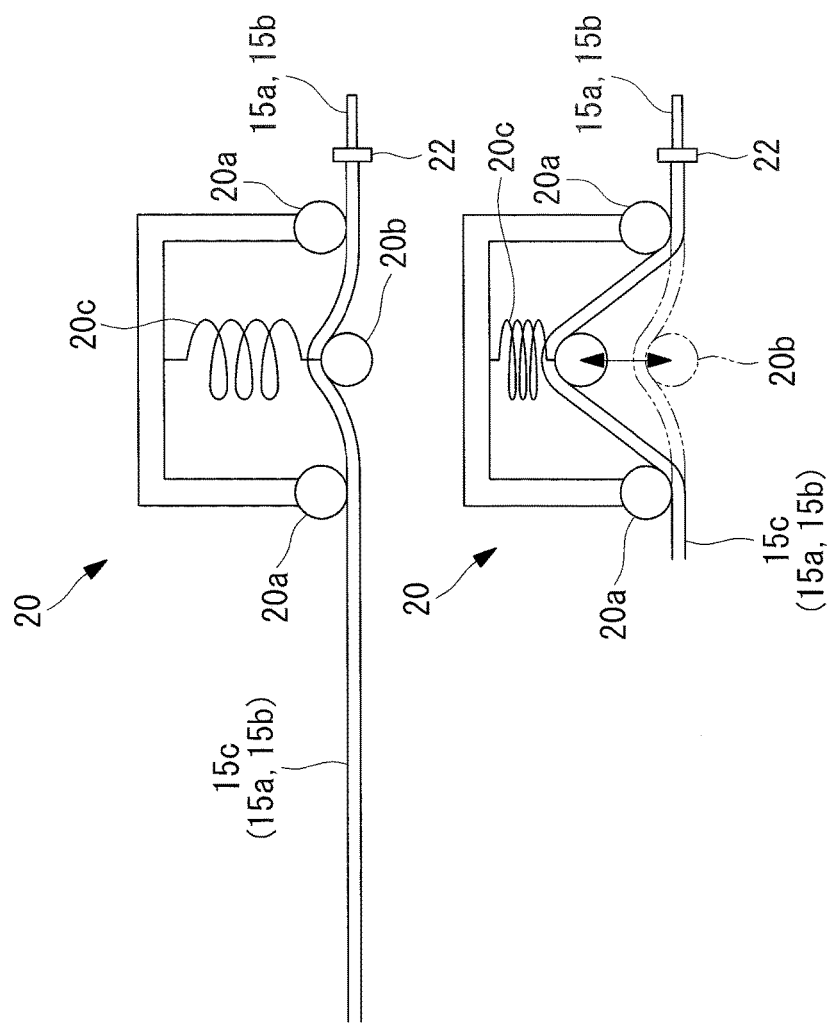
FIG. 14 is a configuration diagram of a sheath-tension adjusting mechanism provided in a manipulator system according to a fourth embodiment of the present invention.

As shown in FIG. 14, the sheath-tension adjusting mechanism 20 includes two fixed pulleys 20a and one movable pulley 20b. The fixed pulleys 20a are disposed so as to be in contact with the outer circumferential surface of the wire sheath 15c, at positions away from each other in the longitudinal direction of the wire sheath 15c, thus fixing the position of the wire 15a or 15b in the radial direction. The movable pulley 20b is disposed between the two fixed pulleys 20a, and the wire sheath 15c is laid on the outer circumferential surface thereof.

The movable pulley 20b is urged in the radial direction (upward in FIG. 14) of the wire sheath 15c by an urging member 20c so as to pull the wire sheath 15c in the radial direction. Thus, when the sheath tension is decreased, as shown in the lower side in FIG. 14, the amount by which the movable pulley 20b pulls the wire sheath 15c increases, cancelling out the decrease in the sheath tension. In contrast, when the sheath tension is increased, the amount by which the movable pulley 20b pulls the wire sheath decreases, cancelling out the increase in the sheath tension. In this way, the sheath-tension adjusting mechanism 20 maintains the sheath tension constant by adjusting the tension applied to the wire sheaths 15c.

At this time, an increase or decrease of the sheath tension derived from the bending shape of the main section 14 corresponds to the amount of sheath-tension adjustment performed by the sheath-tension adjusting mechanism 20, that is, the amount of travel of the movable pulley 20b in the radial direction of the wire sheath 15c. Hence, the control unit 3 can set a compensation value by using the amount of sheath-tension adjustment performed by the sheath-tension adjusting mechanism 20 (more specifically, the position of the movable pulley 20b in the radial direction of the wire sheath 15c), instead of the actual measurement value of the sheath tension measured by the tension sensors 18a. More specifically, the storage portion 19 stores a table of positions of the movable pulley 20b associated with compensation values. The sheath-tension adjusting mechanism 20 sends the position of the movable pulley 20b to the control unit 3, and the control unit 3 acquires, from the storage portion 19, the compensation value corresponding to the position received from the sheath-tension adjusting mechanism 20.

In this case, according to this embodiment, the sheath tension is maintained constant by the sheath-tension adjusting mechanism 20, which leads to an advantage that the degradation in the bending-movement responsiveness of the bending section 15 due to a decrease in sheath tension can be effectively improved. In addition, by determining the compensation value by using the amount of sheath-tension adjustment, which greatly depends on the bending shape, an advantage can be obtained in that the responsiveness can be efficiently maintained in a good state. Because the other advantages are the same as those obtained according to the first embodiment, the descriptions thereof will be omitted.

Note that, in this embodiment, a wire-travelling-amount detecting portion (not shown) that detects the amount of travel of the wires 15a and 15b may be additionally provided, and the control unit 3 may set a compensation value on the basis of the amount of sheath-tension adjustment performed by the sheath-tension adjusting mechanism 20 and the amount of travel of the wires 15a and 15b detected by the wire-travelling-amount detecting portion. Examples of the wire-travelling-amount detecting portion include sensors denoted by reference signs 28 and 30 in Japanese Unexamined Patent Application, Publication No. 2002-264048.

Figure 15:
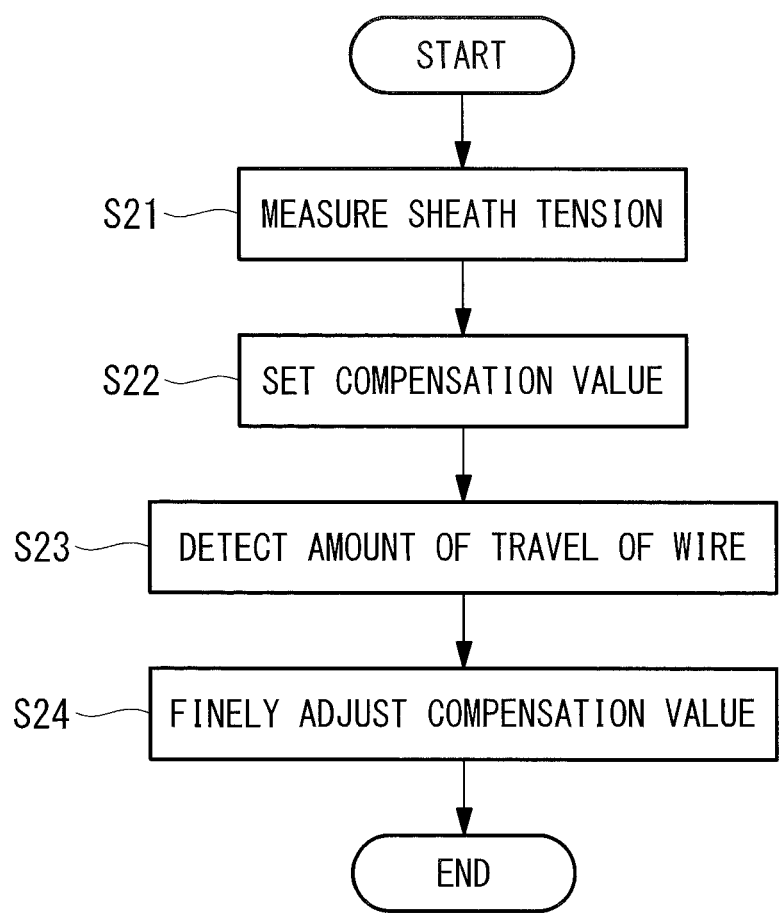
FIG. 15 is a flowchart showing a method for setting a compensation value with the manipulator system in FIG. 14.

In this case, as shown in FIG. 15, the control unit 3 sets a compensation value on the basis of the amount of sheath-tension adjustment performed by the sheath-tension adjusting mechanism 20 (steps S21 and S22) and then makes fine adjustments to the compensation value (step S24) according to the amount of travel of the wires 15a and 15b associated with a change in bending shape of the main section 14 and the bending section 15 (step S23).

In this way, the bending-movement responsiveness of the bending section 15 can be further improved.

Alternatively, instead of the wire-travelling-amount detecting portion, a wire tension detecting portion (not shown) that detects the tension in the wires 15a and 15b may be provided, and the control unit 3 may set a compensation value on the basis of the amount of sheath-tension adjustment performed by the sheath-tension adjusting mechanism 20 and the tensions in the wires 15a and 15b detected by the wire tension detecting portion. Examples of the wire tension detecting portion include tension sensors denoted by reference signs 68 and 70 in Japanese Unexamined Patent Application, Publication No. 2002-264048.

Figure 16:
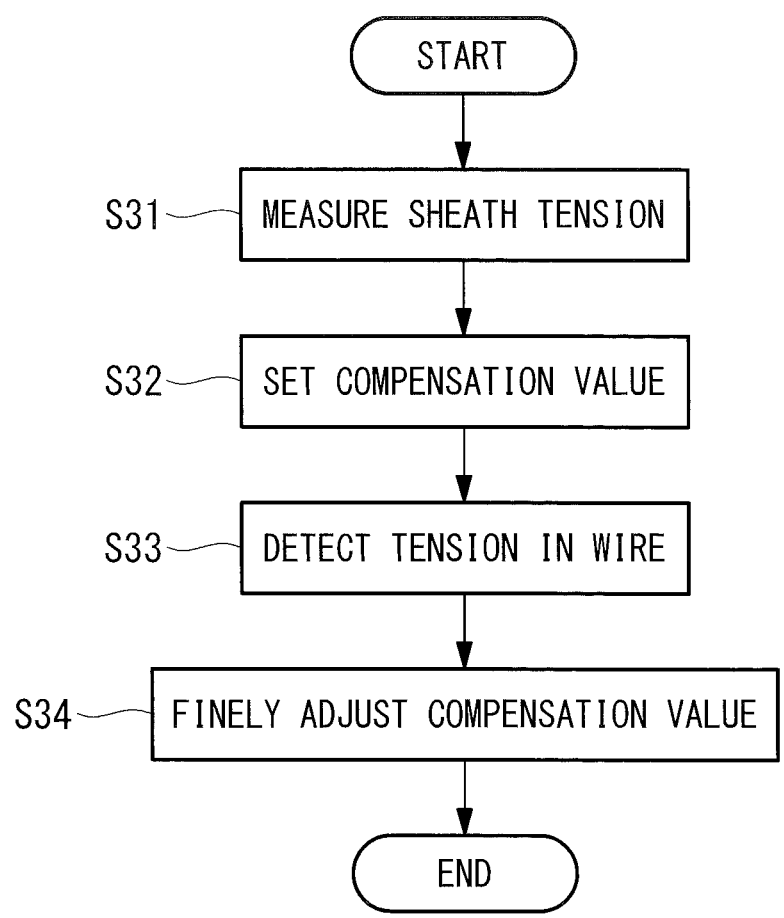
FIG. 16 is a flowchart showing a method for setting a compensation value with a modification of the manipulator system in FIG. 14.

More specifically, as shown in FIG. 16, the control unit 3 sets a compensation value on the basis of the amount of sheath-tension adjustment performed by the sheath-tension adjusting mechanism 20 (steps S31 and S32) and then makes fine adjustments to the compensation value (step S34) according to changes in tensions in the wires 15a and 15b associated with a change in bending shape of the main section 14 and the bending section 15 (step S33).

Also in this way, the bending-movement responsiveness of the bending section 15 can be further improved.

Note that, although an example configuration in which the manipulator 1 and the operation input unit 2 are separate components, and the manipulator 1 is remote-controlled by the operation input unit 2 disposed at a position away from the manipulator 1 has been described in the above-described embodiments and the modifications thereof, the configurations of the manipulator 1 and the operation input unit 2 are not limited thereto, and, for example, the operation input unit 2 may be integrally provided on the rear end of the manipulator 1.

Furthermore, although the manipulator 1 having a flexible main section 14 has been described in the above-described embodiments and the modifications thereof, the main section 14 may be rigid. Also in rigid-type manipulators, the sheath tension greatly depends on the bending shape of the bending section 15, and therefore, there is a strong correlation between the responsiveness of the bending section 15 and the sheath tension. Hence, these embodiments can be suitably applied to the rigid-type manipulators.

From the above-described embodiments and modifications thereof, the following inventions are derived.

The present invention provides a manipulator system including a manipulator that includes an insertion part having an elongated main section and a bending section provided at the distal end of the main section, a bending-section driving portion that makes the bending section perform bending movement, and a linear member inserted through a tubular sheath that is fixed to the main section at at least one end thereof, the linear member connecting the bending section and the bending-section driving portion through the main section and transmitting a driving force generated by the bending-section driving portion to the bending section; an operation input unit via which an operator inputs an operation instruction for the bending section; a control unit that generates a bending control signal for driving the bending-section driving portion according to the operation instruction input to the operation input unit; a sheath-tension detecting portion that detects the tension in the sheath; and a compensation-value setting portion that sets a compensation value for the bending control signal on the basis of the tension in the sheath detected by the sheath-tension detecting portion. The control unit corrects the bending control signal using the compensation value set by the compensation-value setting portion and sends the corrected bending control signal to the bending-section driving portion.

According to the present invention, when the operator inputs an operation instruction to the operation input unit, the control unit sends, to the bending-section driving portion, a bending control signal generated from the operation instruction. When a driving force produced by the bending-section driving portion upon receipt of the bending section control signal is transmitted to the bending section through the linear member, the bending section performs a bending movement according to the operation instruction. In this way, it is possible to remote-control the bending section of the insertion part when positioned, for example, inside the body, by using the operation input unit positioned outside the body.

In this case, the control unit sends the bending control signal to the bending-section driving portion after correcting the bending control signal with the compensation value set by the compensation-value setting portion. The bending-movement responsiveness of the bending section to the operation signal greatly depends on the tension in the sheath, which varies according to the bending shape of the insertion part. The compensation value is set on the basis of the tension in the sheath detected by the sheath-tension detecting portion. In this way, by measuring the tension in the sheath, which greatly depends on the bending shape of the bending section (in the case where the insertion part is a rigid part) or the bending shape of the main section, and by setting a compensation value on the basis of the measurement value, it is possible to precisely compensate for the degradation and variation in the movement responsiveness of the bending section and to constantly obtain good and consistent responsiveness.

In the above-described invention, the sheath-tension detecting portion may include a tension sensor that measures the tension produced in the sheath, and the tension sensor may be provided at a base end portion of the linear member.

With this configuration, the tension sensor may be disposed at a position where it does not influence the design of the other configurations.

In the above-described invention, the sheath-tension detecting portion may include a sheath-tension adjusting mechanism that adjusts the tension to be applied to the sheath such that the tension in the sheath is constant. The sheath-tension detecting portion may measure the amount of tension adjustment performed by the sheath-tension adjusting mechanism, and the compensation-value setting portion may set the compensation value on the basis of the amount of tension adjustment measured by the sheath-tension adjusting mechanism.

With this configuration, even if the bending shape of the insertion part is changed, the tension in the sheath is maintained constant. Thus, it is possible to prevent degradation in responsiveness of the bending section due to decrease in tension in the sheath and to obtain even better responsiveness of the bending section. Furthermore, the amount of sheath-tension adjustment performed by the sheath-tension adjusting mechanism greatly depends on the bending shape of the main section. By using this amount of adjustment of the sheath tension for setting the compensation value, it is possible to efficiency compensate for the degradation and variation in the responsiveness of the bending section.

In the above-described invention, the insertion part may be provided with a passage that defines, via a sheath, a path for the linear member in the insertion part.

Furthermore, in the above-described invention, the manipulator system may further include an outer sheath that accommodates the sheath.

With this configuration, it is possible to reduce degradation and variation in the precision of the measurement values of the sheath tension due to a change in the sheath path and disturbances (e.g., interference between the sheath and another component accommodated in the sheath), which are main causes of variation in responsiveness of the bending section, and to more precisely compensate for the degradation and variation in the responsiveness of the bending section.

In the above-described invention, the manipulator may include a plurality of the linear members inserted through the sheaths, and the plurality of linear members may be bound together, via the sheaths, in the main section.

With this configuration, because variations in friction and slack among the linear members are reduced, it is possible to more precisely compensate for the degradation and variation in the responsiveness of the bending section.

In the above-described invention, the compensation-value setting portion may set the compensation value at a timing specified by the operator.

With this configuration, by the operator specifying the timing for setting the compensation value such that the compensation value is set when good responsiveness of the bending section is required, it is possible to reduce the amount of processing required for setting the compensation value, while maintaining the usability.

In the above-described invention, the compensation-value setting portion may reset the compensation value when a predetermined event is detected.

With this configuration, it is possible to automatically renew the compensation value to the optimum value, every time a predetermined event occurs.

REFERENCE SIGNS LIST 1 slave manipulator (manipulator)
2 master input unit (operation input unit)
3 control unit (compensation-value setting portion)
4 slave arm
5 insertion part
6 treatment tool
7 observation member
8 display
9 master arm
10 insertion-part mounting portion
11 treatment-tool mounting portion
12 bending-section driving portion
13 treatment-tool driving portion
14 main section
15 bending section
15a, 15b wire (linear member)
15c wire sheath (sheath)
15d outer sheath
16 mounting unit
17 treatment tool port
18 sheath-tension detecting portion
18a tension sensor
19 storage portion
20 sheath-tension adjusting mechanism
20a fixed pulley
20b movable pulley
20c urging member
21 passage
22 fixing portion
80 operating table
100 manipulator system
Op operator (operator)

The invention claimed is:
1. A manipulator system comprising:
a manipulator that includes an insertion part having an elongated main section and a bending section provided at a distal end of the main section, a bending-section actuator that makes the bending section perform bend- ing movement, and a linear member inserted through a tubular sheath that is fixed to the main section at at least one end thereof, the linear member connecting the bending section and the bending-section actuator through the main section and transmitting a driving force generated by the bending-section actuator to the bending section, the tubular sheath extending from a proximal end of the elongated main section and terminating at a proximal end of the bending section;

an operation input via which an operator inputs an operation instruction for the bending section;

a tension sensor that measures tension produced in the sheath, the tension sensor being mounted to a proximal end of the tubular sheath and being fixed to the elongated main section by an elastic spring; and a controller configured to:
- generate a bending control signal for driving the bending-section actuator according to the operation instruction input to the operation input;
- set a compensation value for the bending control signal on the basis of the tension in the sheath detected by the tension sensor; and correct the bending control signal using the set compensation value and send the corrected bending control signal to the bending-section actuator.

2. The manipulator system according to claim 1, further comprising a sheath-tension adjusting mechanism that adjusts the tension to be applied to the sheath such that the tension in the sheath is constant,
- the tension sensor measures the amount of tension adjustment performed by the sheath-tension adjusting mechanism, and
- the controller sets the compensation value on the basis of the amount of tension adjustment measured by the sheath-tension adjusting mechanism.

3. The manipulator system according to claim 1, wherein the insertion part is provided with a passage that defines, via a sheath, a path for the linear member in the insertion part.

4. The manipulator system according to claim 1, further comprising an outer sheath that accommodates the sheath.

5. The manipulator system according to claim 1, wherein
- the manipulator includes a plurality of the linear members inserted through the sheaths, and
- the plurality of linear members are bound together, via the sheaths, in the main section.

6. The manipulator system according to claim 1, wherein the controller sets the compensation value at a timing specified by the operator.

7. A manipulator system according to claim 1, wherein the controller resets the compensation value when a predetermined event is detected.

* * * * *